(12) United States Patent
Gudeman et al.

(10) Patent No.: US 10,955,336 B2
(45) Date of Patent: Mar. 23, 2021

(54) GAS SENSOR COMPRISING A ROTATABLE FABRY-PEROT MULTILAYER ETALON

(71) Applicant: Innovative Micro Technology, Goleta, CA (US)

(72) Inventors: Christopher S. Gudeman, Lompoc, CA (US); Jaquelin K. Spong, Mount Jackson, VA (US)

(73) Assignee: Innovative Micro Technology, Goleta, CA (US)

( * ) Notice: Subject to any disclaimer, the term of this patent is extended or adjusted under 35 U.S.C. 154(b) by 0 days.

(21) Appl. No.: 16/105,448

(22) Filed: Aug. 20, 2018

(65) Prior Publication Data

US 2019/0064060 A1 Feb. 28, 2019

Related U.S. Application Data

(60) Provisional application No. 62/550,571, filed on Aug. 26, 2017.

(51) Int. Cl.
| | |
|---|---|
| *G01J 3/26* | (2006.01) |
| *G01J 3/42* | (2006.01) |
| *G01N 21/3504* | (2014.01) |
| *G01N 21/25* | (2006.01) |
| *G01N 33/00* | (2006.01) |
| *G01N 21/35* | (2014.01) |
| *G01N 21/03* | (2006.01) |
| *G01J 3/12* | (2006.01) |

(52) U.S. Cl.
CPC ............ *G01N 21/3504* (2013.01); *G01J 3/26* (2013.01); *G01J 3/42* (2013.01); *G01N 21/255* (2013.01); *G01N 33/004* (2013.01); *G01J 2003/1234* (2013.01); *G01J 2003/1243* (2013.01); *G01J 2003/1247* (2013.01); *G01N 21/031* (2013.01); *G01N 2021/3595* (2013.01); *G01N 2201/0636* (2013.01)

(58) Field of Classification Search
CPC ....... G01J 2003/1226; G01J 2003/1234; G01J 2003/1243; G01J 3/26; G01J 3/42; G01N 2201/0636; G01N 21/3504
USPC ..................................... 356/454; 250/339.13
See application file for complete search history.

(56) References Cited

U.S. PATENT DOCUMENTS

| | | | | |
|---|---|---|---|---|
| 4,743,114 A * | 5/1988 | Crane, Jr. | ................ | G01J 9/02 356/454 |
| 5,214,494 A * | 5/1993 | Inaba | ........................ | G01J 1/04 250/226 |
| 5,844,734 A * | 12/1998 | Sharp | ........................ | G01J 3/26 359/885 |
| 6,747,742 B1 * | 6/2004 | Verma | ........................ | G01J 3/02 356/451 |
| 6,816,636 B2 * | 11/2004 | Cole | ........................ | G01J 3/26 349/198 |

(Continued)

OTHER PUBLICATIONS

Douglas W. White et al., Laboratory spectra of CO2 vibrational modes in planetary ice analogs, Icarus 221 (2012), pp. 1032-1042.*

*Primary Examiner* — Allen C. Ho
(74) *Attorney, Agent, or Firm* — Jaquelin K. Spong

(57) ABSTRACT

Systems and methods for forming a compact gas sensor include a multilayer etalon as a wavelength discriminating element. The position of the etalon may be adjusted to tune its transmission profile. And embodiment directed to carbon dioxide detection is described.

17 Claims, 7 Drawing Sheets

(56) References Cited

U.S. PATENT DOCUMENTS

| | | | |
|---|---|---|---|
| 7,050,215 B1 * | 5/2006 | Johnson | G01J 3/42 359/260 |
| 7,319,560 B2 * | 1/2008 | Gunning | G01J 3/26 356/519 |
| 7,864,326 B2 * | 1/2011 | Cox | G01N 21/031 356/454 |
| 8,977,086 B2 * | 3/2015 | DeCorby | G02B 6/02304 385/43 |
| 9,134,175 B2 * | 9/2015 | Matsushita | G01J 3/0205 |
| 9,268,144 B2 * | 2/2016 | Rissanen | G02B 27/142 |
| 9,270,898 B2 * | 2/2016 | Funamoto | H04N 5/243 |
| 9,335,209 B2 * | 5/2016 | Matsuno | G01J 1/0488 |
| 9,347,831 B2 * | 5/2016 | Funamoto | G01J 3/2823 |
| 9,372,114 B2 * | 6/2016 | Carr | G01J 3/26 |
| 9,426,380 B2 * | 8/2016 | Funamoto | G01J 3/26 |
| 9,651,770 B2 * | 5/2017 | Shinto | G02B 1/11 |
| 9,658,446 B2 * | 5/2017 | Hirokubo | G02B 26/001 |
| 9,664,563 B2 * | 5/2017 | Lucey | G01J 3/14 |
| 9,678,259 B2 * | 6/2017 | Matsuno | G02B 5/284 |
| 9,721,195 B2 * | 8/2017 | Nozawa | H04N 1/00023 |
| 9,753,199 B2 * | 9/2017 | Nishimura | G02B 5/28 |
| 9,766,125 B2 * | 9/2017 | Gomi | G01J 3/2823 |
| 9,797,774 B2 * | 10/2017 | Sano | G01J 3/0272 |
| 9,823,129 B2 * | 11/2017 | Kuri | G01J 3/0229 |
| 9,826,172 B2 * | 11/2017 | Funamoto | G01J 3/10 |
| 9,835,492 B2 * | 12/2017 | Nishimura | G01J 3/2823 |
| 9,857,221 B2 * | 1/2018 | Matsushita | G01J 3/0213 |
| 9,880,055 B2 * | 1/2018 | Sano | G01J 3/0208 |
| 9,910,262 B2 * | 3/2018 | Hirokubo | G02B 26/001 |
| 9,939,629 B2 * | 4/2018 | Matsushita | G02B 5/22 |
| 9,971,143 B2 * | 5/2018 | Nishimura | G02B 26/001 |
| 9,976,899 B2 * | 5/2018 | Nishimura | G01J 3/021 |
| 9,998,633 B2 * | 6/2018 | Kuri | G01J 3/463 |
| 10,066,996 B2 * | 9/2018 | Zhao | G01J 3/26 |
| 10,088,362 B2 * | 10/2018 | Varpula | G01J 3/26 |
| 10,156,713 B2 * | 12/2018 | Matsushita | G02B 27/0012 |
| 10,184,832 B2 * | 1/2019 | Shibayama | G01J 3/26 |
| 10,247,609 B2 * | 4/2019 | Kanai | G01J 3/027 |
| 10,473,912 B2 * | 11/2019 | Nozawa | G01J 3/0291 |
| 10,485,464 B2 * | 11/2019 | Sakurai | G01N 21/01 |

* cited by examiner

Fig. 3 Multi pass system

Fig. 5A

| Layer | Material | Refractive Index | Extinction Coefficient | Optical Thickness (FWOT) | Physical Thickness (nm) |
|---|---|---|---|---|---|
| Medium | Air | 1.00000 | 0.00000 | | |
| 1 | Si (CRYSTAL) | 3.53800 | 0.00000 | 0.22639828 | 264.95 |
| 2 | SiO2 | 1.37795 | 0.00000 | 0.25301820 | 784.60 |
| 3 | Si (CRYSTAL) | 3.53800 | 0.00000 | 0.25519482 | 308.91 |
| 4 | SiO2 | 1.37795 | 0.00000 | 0.20095053 | 623.14 |
| 5 | Si (CRYSTAL) | 3.53800 | 0.00000 | 0.26918018 | 325.81 |
| 6 | SiO2 | 1.37795 | 0.00000 | 0.15759636 | 488.79 |
| 7 | Si (CRYSTAL) | 3.53800 | 0.00000 | 0.11384091 | 137.80 |
| 8 | SiO2 | 1.37795 | 0.00000 | 0.10662074 | 330.63 |
| 9 | Si (CRYSTAL) | 3.53800 | 0.00000 | 0.27018585 | 327.05 |
| 10 | SiO2 | 1.37795 | 0.00000 | 0.15510069 | 480.96 |
| 11 | Si (CRYSTAL) | 3.53800 | 0.00000 | 0.34147236 | 413.35 |
| 12 | SiO2 | 1.37795 | 0.00000 | 0.19751081 | 612.48 |
| 13 | Si (CRYSTAL) | 3.53800 | 0.00000 | 0.36325227 | 439.71 |
| 14 | SiO2 | 1.37795 | 0.00000 | 0.16499504 | 511.65 |
| 15 | Si (CRYSTAL) | 3.53800 | 0.00000 | 0.13999235 | 169.46 |
| 16 | SiO2 | 1.37795 | 0.00000 | 0.06095077 | 187.15 |
| 17 | Si (CRYSTAL) | 3.53800 | 0.00000 | 0.10862939 | 131.74 |
| 18 | SiO2 | 1.37795 | 0.00000 | 0.17074336 | 529.47 |
| 19 | Si (CRYSTAL) | 3.53800 | 0.00000 | 0.20633492 | 249.76 |
| 20 | SiO2 | 1.37795 | 0.00000 | 0.22174676 | 687.63 |
| Substrate | Si (CRYSTAL) | 3.53800 | 0.00000 | | |

Fig. 5B

| Layer | Material | Refractive Index | Extinction Coefficient | Optical Thickness (FWOT) | Physical Thickness (nm) |
|---|---|---|---|---|---|
| Medium | Air | 1.00000 | 0.00000 | | |
| 1 | Ag | 0.49000 | 14.40000 | 0.00720000 | 30.00 |
| 2 | SiO2 | 1.43807 | 0.00000 | 1.07895369 | 1500.00 |
| 3 | Ag | 0.49000 | 14.40000 | 0.00720000 | 30.00 |
| Substrate | Glass | 1.49447 | 0.00000 | | |

Fig. 5

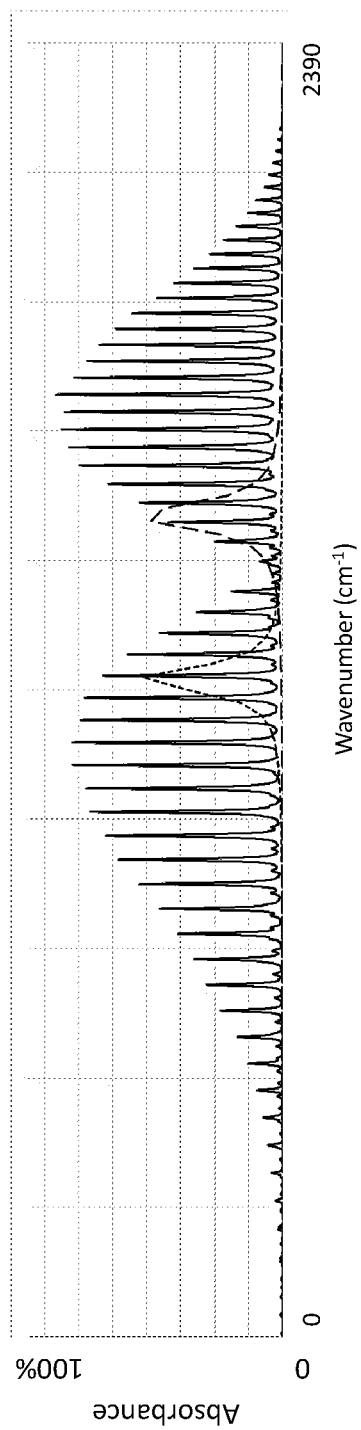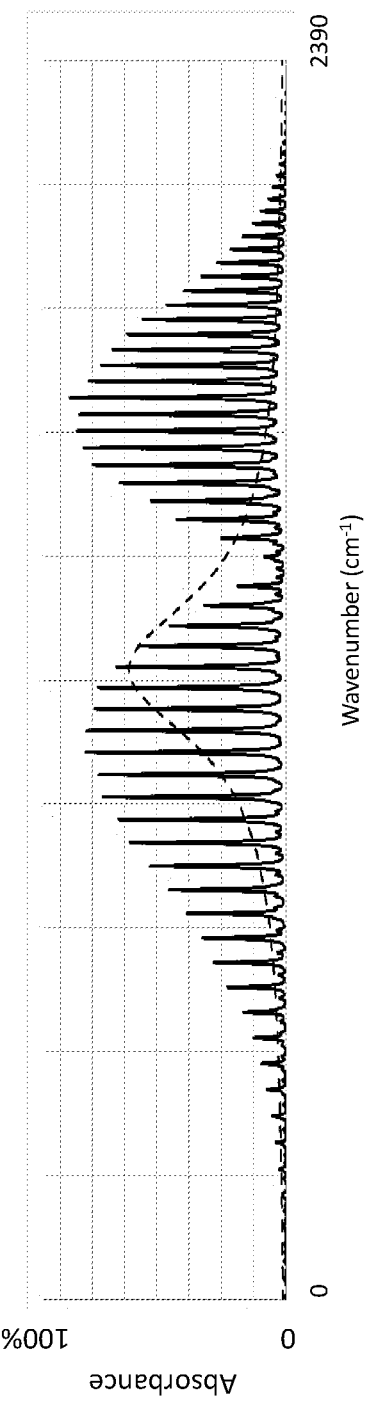

GAS SENSOR COMPRISING A ROTATABLE FABRY-PEROT MULTILAYER ETALON

CROSS REFERENCE TO RELATED APPLICATIONS

This nonprovisional US Patent Application claims priority to U.S. Provisional Application Ser. No. 62/550,571, filed Aug. 26, 2017 and incorporated by reference in its entirety.

STATEMENT REGARDING FEDERALLY SPONSORED RESEARCH

Not applicable.

STATEMENT REGARDING MICROFICHE APPENDIX

Not applicable.

BACKGROUND

This invention relates to a gas sensing device.

Gas sensors require high sensitivity and high specificity, two factors that are often in opposition, since a very sensitive system will likely be sensitive to many gases. But high sensitivity is extremely important for safety. For example, exposure to 1 part per million of CO in the atmosphere will cause headaches in 10 minutes and irreversible brain damage 60 minutes.

Chemical receptor systems that provide very high sensitivity to CO, often have a low level sensitivity to $CO_2$, which is far more abundant. A rather high concentration of $CO_2$ can therefore create a false positive readout of a sensor that is targeting CO detection. Thus, distinguishing between harmful and benign gases is a problem.

Chemical receptor systems can also become contaminated, which causes a loss in sensitivity and consequent risk to personnel. This situation can result in a false negative readout, and thus is quite dangerous.

Gas sensors fall into several categories, based on the detection mechanism that they employ. Generally, these include the following:

1) Chemical receptors for specific capture of the target molecule. Here, a chemical compound is covalently bonded to a substrate, which is part of the sensor. Within the molecular structure of this chemical compound is a functional group of atoms that will link with a specific type of target molecule. If a target molecule attaches to the chemical receptor, a change is recorded in the substrate voltage, current, temperature, conductivity, magnetic moment, optical absorbance or reflection. These signals are often very weak and similar levels of a given signal can arise from a variety of molecular species. This leads to inaccuracies, false positives and false negatives.
2) Resonant beam structures to determine the mass of the molecule. The resonant beam structure is often used with the chemical receptor. These beams are very low in mass so the attachment of a population of target molecules can significantly affect the mass and thus significantly change the frequency of its fundamental mechanical resonance. The shift in resonant frequency is generally small and the quantity of target molecules and their chemical structure are factors that are difficult to separate. This measurement can thus also lead to incorrect identification. Finally, strongly adhered target molecules can be difficult to desorb following the sensing measurement.
3) Sensors that combust the target species and measure its exothermicity. Most gaseous molecular species can be oxidized, which means they can be burned or combusted in an oxygen environment, such as air. A few notable exceptions (non-combustible compounds) include $O_2$, $N_2$, $CO_2$, Ar, and $H_2O$, which are the constituents of air. Therefore, the heat generated during the chemical reaction of combustion is a means of sensing combustible trace impurities in air. In other words, because the dominant constituents of air do not combust, the trace species can more easily be detected without interference by measuring the heat generated. This measurement can be used to identify the impurity. For example, the heat generated during combustion of CO is far less than the heat generated by burning benzene, heptane, or tri-nitro-toluene (TNT), for example. All of the latter, however, have similar heat generation per unit mass of target species. Also the quantity of heat generated is extremely low, making accurate detection difficult. To ignite the target molecules, the system for combustion must operate at very high temperature, thus leading to very short lifetime and poor reliability.
4) Chemical Field Effect Transistors (Chem-FET). If the gate electrode of a field effect transistor (FET) is replaced by a population of covalently-bonded chemical receptors, the trans-conductance of the FET will change in the presence of molecules that attach to the receptors. Intrinsically the FET provides gain and thus this method can be very sensitive. However, attached target molecules can be difficult to detach following a sensing episode, since high temperature, which can adversely affect the FET, is required to desorb attached molecules. Strongly bonded contaminants can survive even the highest temperatures that can be practically applied in the field of use.
5) Combinations of the above. Due to the limitations outlined above, it has been found useful to combine those methods into a system. This can greatly reduce the risk of false positive and false negative responses, although the cost and complexity of the system are increased.

Accordingly, a new technology is needed for sensing these dangerous compounds in homes, offices and industrial settings. Ideally this technology is small, inexpensive, robust and highly sensitive.

SUMMARY

The device and method described here uses high resolution infrared spectroscopy to detect and identify small gas molecules. The spectrum of thousands of small molecules is well documented. These spectra provide a fingerprint of each compound that can be used to unambiguously identify the compound, with no chance of falsely assigning the measured spectrum.

The device described here uses a broad spectrum infrared emitter to emit radiation over a range of wavelengths. The frequency spectrum may be chosen to overlap one or more absorption features of a target gas impurity in the air. Frequencies within that absorption band will be strongly attenuated by the gaseous sample between the emitter and the detector.

A frequency selector is then used to separate the wavelengths of light from the broadband emitter. The device described here uses a multilayer Fabry-Perot type etalon to separate the frequencies and provide high spectral resolution. By tilting or changing the position of the etalon, its passband can be tuned. Accordingly, the adjustable etalon can be used as a frequency or color analyzer.

A detector may then be used at the end of the path of the radiation from the emitter through the etalon and gas sample. The detector may be, for example, a photodiode, avalanche detector or photomultiplier tube. The detector may measure the amount of radiation transmitted through the gas and the etalon, as a function of wavelength or frequency. Comparison of the results with the known, documented absorption spectra may unambiguously identify the gas species present.

Accordingly, described here is a gas sensing device. The gas sensing device may include a broad spectrum infrared emitter, a sample of a gas, a multilayer etalon with a transmission profile that transmits wavelengths of light from the broad spectrum infrared emitter within a passband, a positioner that adjusts the position of the etalon with respect to the emitter, so as to tune the passband of the etalon, and a detector that detects the amount of light transmitted through the etalon and the gas sample. The broad spectrum emitter may be the sun.

Also described is a method of sensing a gas. The method may include providing radiation from a broad spectrum emitter, applying the radiation to a sample of a gas, transmitting the radiation in the passband of a multilayer etalon with a transmission profile that transmits wavelengths of light from the broad spectrum infrared emitter within a passband, and detecting the amplitude of the transmitted radiation.

These and other features and advantages are described in, or are apparent from, the following detailed description.

BRIEF DESCRIPTION OF THE DRAWINGS

Various exemplary details are described with reference to the accompanying drawings, which however, should not be taken to limit the invention to the specific embodiments shown but are for explanation and understanding only.

FIGS. 5A and 5B show tables of the design of an etalon structure operating at about 2300 wavenumbers. FIG. 5A shows a table detailing an etalon structure consisting of 20 layers of transparent thin dielectric films arranged in a Bragg stack, FIG. 5B shows a table detailing an etalon structure consisting of thin silver films, where the thickness of silver is on the order of one skin depth;

FIG. 7A shows the overlap of the 20 layer etalon transmission profile with the $CO_2$ absorption spectrum. FIG. 7B shows the overlap of the silver etalon transmission profile with the $CO_2$ absorption spectrum.

It should be understood that the drawings are not necessarily to scale, and that like numbers maybe may refer to like features.

DETAILED DESCRIPTION

The device and method described here uses high resolution infrared spectroscopy to detect and identify small gas molecules. The spectrum of thousands of small molecules is well documented. These spectra provide a fingerprint of each compound that can be used to unambiguously identify the compound, with no chance of falsely assigning the measured spectrum.

To provide high sensitivity, the spectrometer must possess several aspects:

1) A high resolution monochromator. Generally gratings or prisms are used to disperse the incident light into it component wavelengths. In this case a multi-stack Fabry-Perot etalon is micro-fabricated at wafer level and diced to form a transmissive wavelength selection device.
2) A long absorption path. The long path in this case may be the entire atmosphere.
3) A bright light source. In this case, the source may the sun.
4) A sensitive infrared detector. Numerous semiconductor detector technologies exist including photodiodes and photomultiplier tubes, for example.
5) A digital spectral database that can be quickly compared to the observed spectrum for identification and quantification.

Described below is a system that can detect $CO_2$ with very high specificity and sensitivity. This is intended to be an example and should not be taken to limit the invention to only $CO_2$ applications. The systems and methods described here may be used to detect a wide variety of gaseous species present in an environment.

Figures 1A, 1B:
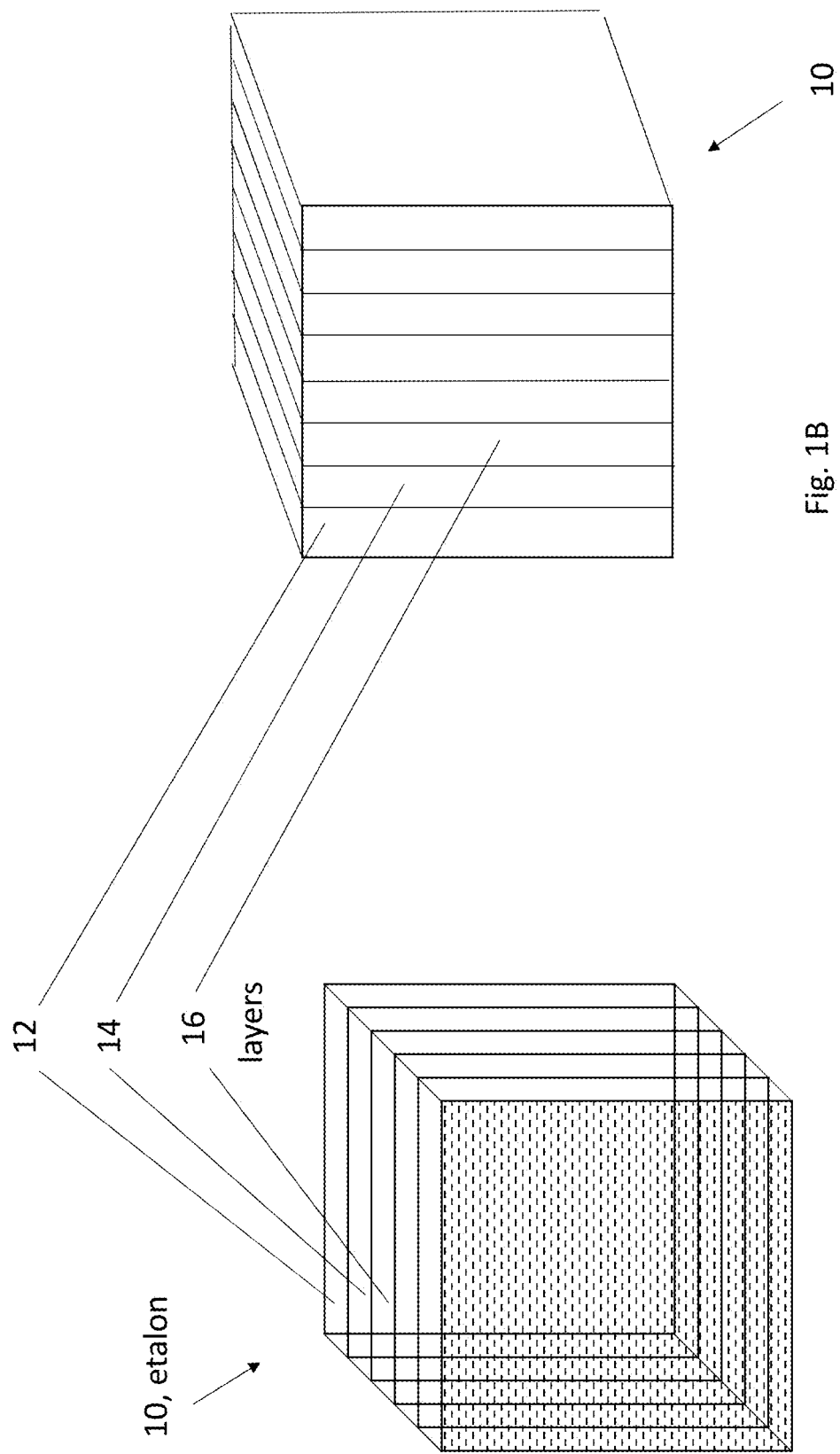
FIG. 1A is an illustrative exemplary perspective three-dimensional view of an etalon wavelength selector.
FIG. 1B is a different perspective three-dimensional view of the etalon wavelength selector.

FIG. 1 is an illustrative exemplary view of an etalon 10 wavelength selector or discriminating element using a multilayer architecture. FIG. 1A is an illustrative perspective three-dimensional view of an etalon 10 wavelength selector; FIG. 1B is a different perspective three-dimensional view of the etalon 10 wavelength selector. The layers 12, 14 and 16 are chosen with a thickness designed to impact the transmission spectrum, i.e. using destructive or constructive interference to define or enhance the passband characteristics. In particular, knowing the refractive index of a material and with the precise control of film thicknesses (such control as is available when quartz crystal micro balances are used during deposition, for example), it is possible to design a multilayer structure where the reflected wave phase and amplitude perfectly matches the incoming wave phase and amplitude, and thus the transmitted radiative power s maximized for certain wavelengths. Accordingly, such multilayer structures may pass only a very narrow band of wavelengths, and thus can be used as a wavelength selector or discriminating element.

The etalon 10 may be of the Fabry-Perot sort, and may be used for the purpose of wavelength selection. A very high resolution Fabry-Perot etalon can be realized by stacking many (>~20) layers of thin (<1 micron), transparent films on a suitably transparent substrate. Because these films have different refractive indices, for example $n(Si)=3.5$ and $n(SiO_2)=1.45$, each interface between layers will cause reflection. By appropriate selection of the layer thicknesses, the number of layers and the refractive indices of each layer, a very narrow wavelength band of light traveling in the forward direction can be made to constructively interfere, while all other wavelengths are reflected.

Alternatively an etalon 10 can be constructed from very thin films of silver. In this case the thickness of the silver films should be on the order of the skin depth of silver.

The etalon 10 may be used to tune the wavelength transmitted from the broadband source and applied to the gas sample 40 and transmitted to the detector 30. By tilting the etalon 10 with respect to the optical axis, the passband of the etalon 10 may be swept to longer frequencies and through the absorption features of the gas sample 40. Upon tuning the etalon 10 to the precise wavelength of an absorption feature, a reduction in the transmitted intensity may be measured by the detector 30. The operation of this gas sensor using an etalon 10 is described further below.

Figure 2:
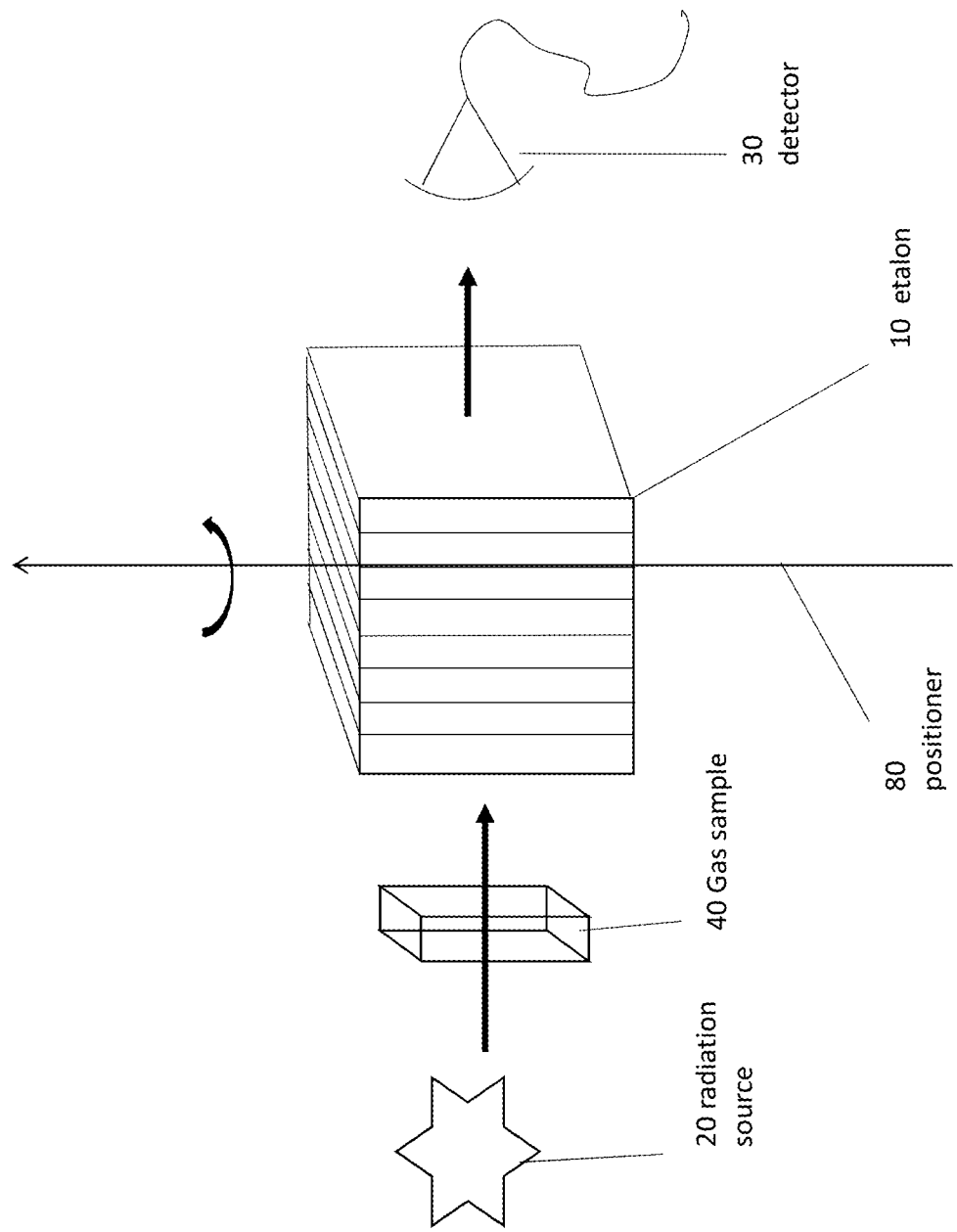
FIG. 2 is an illustrative exemplary view of gas sensor using the etalon wavelength selector.

FIG. 2 is an illustrative exemplary view of gas sensor using the etalon 10 wavelength selector. A radiation source 20 may be placed in front of a gas sample 40, which absorbs certain wavelengths of the light. The light source 20 may be relatively broadband, overlapping a number of the absorption features of the gas sample 40. An etalon 10 determines the radiation frequencies which are passed, and a detector 30 measures the amplitude of the radiation.

A positioner 80 may adjust the rotational orientation of the etalon 10 with respect to the optical axis as shown in FIG. 2. In particular, the etalon 10 may be mounted on a movable stage which may rotate the etalon 10 about a rotational axis. The rotational axis may be perpendicular to the optical axis as shown. Any of a number of rotary actuators, stepper motors, and the like may be used for this purpose. Alternatively, the etalon 10 may be suspended from above. By rotating the etalon 10 about a rotational axis, the passband of the etalon 10 may be moved along the frequency (or wavelength spectrum. When the rotation is zero degrees, (i.e. the front surface of the first film is perpendicular to the optical axis), the etalon 10 passband may be at it's shortest wavelength (highest frequency). Tilting the etalon 10 about the rotational axis may shift the etalon 10 passband to longer wavelengths (lower frequencies), because the effective path length within the etalon 10 layers is longer.

Figure 3:
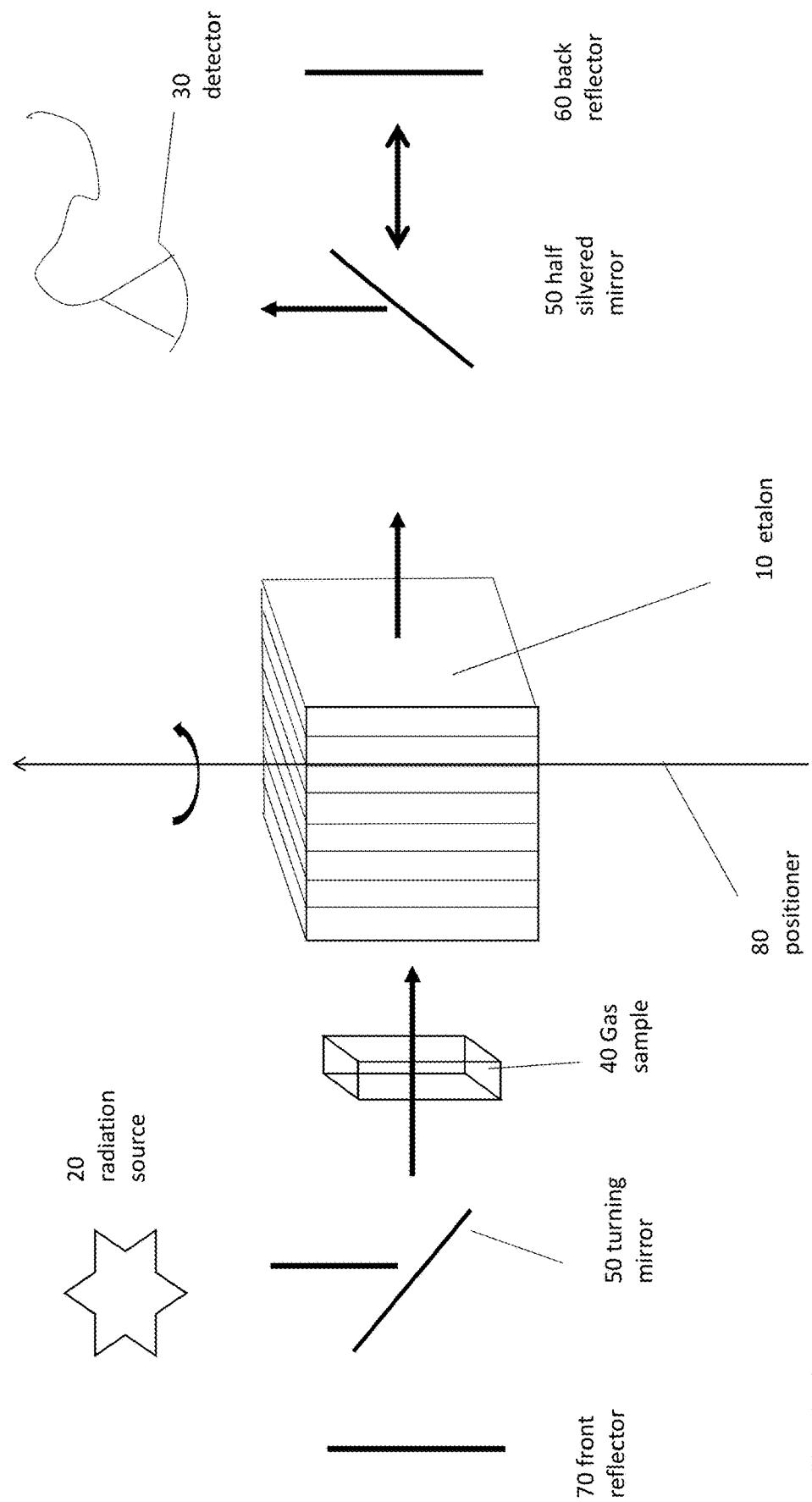
FIG. 3 is an illustrative exemplary view of gas sensor using the etalon wavelength selector in a multipass configuration.

FIG. 3 is an illustrative exemplary view of gas sensor using the etalon wavelength selector in a multipass configuration. In FIG. 3, a radiation source 20 may again be placed in front of a gas sample 40, which absorbs certain wavelengths of the light. However, in this multipass configuration, the radiation is injected into a cavity by a turning mirror 50, wherein the cavity is defined by a front reflector 70 and a back reflector 60. Similarly, another half-silvered turning mirror 50 may direct the radiation to a detector 30.

Again, the radiation source 20 may be relatively broadband, overlapping a number of the absorption features of the gas sample 40. An etalon 10 determines the radiation frequencies which are passed, and a detector 30 measures the amplitude of the radiation as a function of wavelength.

As in FIG. 3, a positioner 80 may adjust the rotational orientation of the etalon 10 with respect to the optical axis as shown in FIG. 3. In particular, the etalon 10 may be mounted on a movable stage which may rotate the etalon 10 about a rotational axis. The rotational axis may be perpendicular to the optical axis as shown. Any of a number of rotary actuators, stepper motors, and the like may be used for this purpose. Alternatively, the etalon 10 may be suspended from above.

Figure 4:
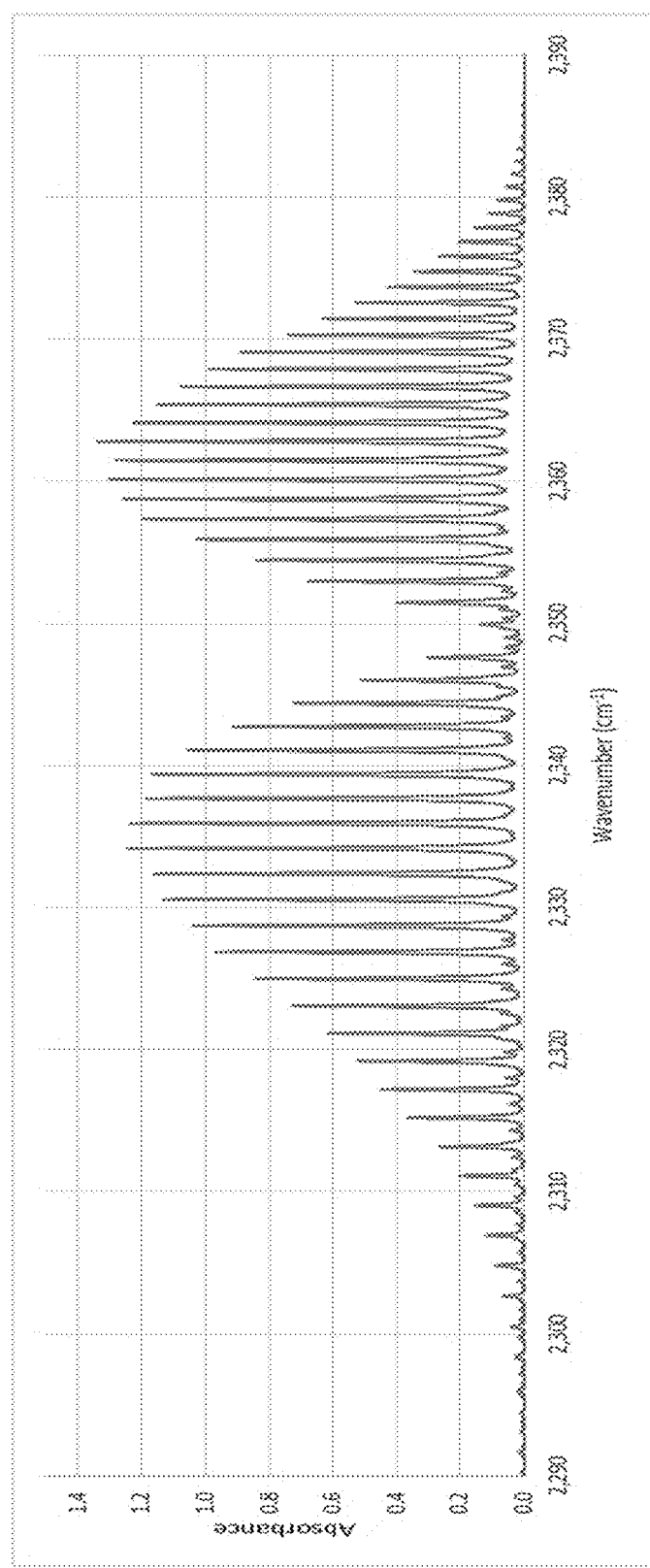
FIG. 4 shows the absorption spectrum of $CO_2$.

FIG. 4 shows the absorption spectrum of carbon dioxide ($CO_2$) in the infrared. Each absorption peak corresponds to a quantum mechanical excitation of the $CO_2$ molecule from a rotational state in the ground vibrational state to a rotational state in the $1^{st}$ excited vibrational state. Because the $CO_2$ molecule is so simple, its spectrum is also quite simple. The molecule absorbs the incident light, which in this case is in the infrared, and which induces the transition. The energy may be re-radiated at a shifted frequency.

Some energy is removed from the radiation because of absorption by the gas. This occurs at exactly the wavelength of light that matches the energy of the transition. The science of measuring the radiation energy loss as it passes through a sample is known as absorption spectroscopy. The peaks in a spectrum are often referred to as lines due to older spectroscopic methods that used a grating as a monochromator and photographic film as a detector. The light diffracted from the grating would expose a series of lines on the photographic emulsion. Unfortunately, for very high resolution, classical monochromators can be several meters long so that the individual wavelengths can be adequately separated by from each other.

Excellent laboratory infrared spectroscopy is generally carried out using a Fourier Transform Infrared Spectrometer (FTIR). The spectrum shown in FIG. 4 was acquired with an FTIR. An FTIR uses a Michelson Interferometer, which is capable of high resolution dispersion of the wavelengths, but as increased resolution is needed, increasingly longer lengths of the optics are required. These systems are generally 1 meter in length.

For unambiguous gas sensing, a means to select wavelengths with high resolution in a very small (<1 cm) package is needed. This monochromator can then be coupled with a light source and a radiation detector to complete the gas sensor spectrometer.

As mentioned previously, a high resolution Fabry-Pert etalon may be constructed by stacking many (>~20) layers of thin (<1 micron), transparent films on a suitably transparent substrate. Because these films have different refractive indices, for example n(Si)=3.5 and n($SiO_2$)=1.45, each interface between layers will cause reflection. By appropriate selection of the layer thicknesses, the number of layers and the refractive indices of each layer, a very narrow wavelength band of light traveling in the forward direction can be made to constructively interfere, while all other wavelengths are reflected. Alternatively, an etalon can be constructed from very thin films of silver. In this case, the thickness of the silver films should be on the order of the skin depth of silver.

The skin depth is a term of art that refers to the depth of a conductor which carries the predominant portion of an alternating current flowing in the conductor. Skin effect is the tendency of an alternating electric current (AC) to become distributed within a conductor such that the current density is largest near the surface of the conductor, and decreases with greater depths in the conductor. The electric current flows mainly at the "skin" of the conductor, between the outer surface and a level called the skin depth. The skin effect causes the effective resistance of the conductor to increase at higher frequencies where the skin depth is smaller, thus reducing the effective cross-section of the conductor. The skin effect is due to opposing eddy currents induced by the changing magnetic field resulting from the alternating current. At 60 Hz in copper, the skin depth is about 8.5 mm. At high frequencies the skin depth becomes much smaller. Because the interior of a large conductor carries so little of the current, tubular conductors such as pipe can be used to save weight and cost.

For alternating current, the current density decreases exponentially from the surface towards the inside. The skin depth, $\delta$, is defined as the depth where the current density is just 1/e (about 37%) of the value at the surface; it depends on the frequency of the current and the electrical and magnetic properties of the conductor.

For the 20 layer stack etalon and the silver etalon examples, the design of an etalon filter stack is shown in FIG. 5A, B, which are also reproduced below. FIG. 5A shows the thin film stack and FIG. 5B shows the silver etalon multilayer construction.

| Layer | Material | Refractive Index | Extinction Coefficient | Optical Thickness (FWOT) | Physical Thickness (nm) |
|---|---|---|---|---|---|
| Medium | Air | 1.00000 | 0.00000 | | |
| 1 | Si (CRYSTAL) | 3.53000 | 0.00000 | 0.23539828 | 284.95 |
| 2 | SiO2 | 1.37795 | 0.00000 | 0.25301830 | 784.60 |
| 3 | Si (CRYSTAL) | 3.53000 | 0.00000 | 0.25519482 | 308.91 |
| 4 | SiO2 | 1.37795 | 0.00000 | 0.20095053 | 623.14 |
| 5 | Si (CRYSTAL) | 3.53000 | 0.00000 | 0.26916018 | 325.81 |
| 6 | SiO2 | 1.37795 | 0.00000 | 0.15759636 | 488.70 |
| 7 | Si (CRYSTAL) | 3.53000 | 0.00000 | 0.11384081 | 137.80 |
| 8 | SiO2 | 1.37795 | 0.00000 | 0.10662074 | 330.63 |
| 9 | Si (CRYSTAL) | 3.53000 | 0.00000 | 0.27018565 | 327.05 |
| 10 | SiO2 | 1.37795 | 0.00000 | 0.15510068 | 480.96 |
| 11 | Si (CRYSTAL) | 3.53000 | 0.00000 | 0.34147236 | 413.35 |
| 12 | SiO2 | 1.37795 | 0.00000 | 0.19751081 | 612.48 |
| 13 | Si (CRYSTAL) | 3.53000 | 0.00000 | 0.36325227 | 439.71 |
| 14 | SiO2 | 1.37795 | 0.00000 | 0.16499504 | 511.65 |
| 15 | Si (CRYSTAL) | 3.53000 | 0.00000 | 0.13999235 | 169.46 |
| 16 | SiO2 | 1.37795 | 0.00000 | 0.06035077 | 187.15 |
| 17 | Si (CRYSTAL) | 3.53000 | 0.00000 | 0.10882999 | 131.74 |
| 18 | SiO2 | 1.37795 | 0.00000 | 0.17074306 | 529.47 |
| 19 | Si (CRYSTAL) | 3.53000 | 0.00000 | 0.20633492 | 249.76 |
| 20 | SiO2 | 1.37795 | 0.00000 | 0.22174676 | 687.63 |
| Substrate | Si (CRYSTAL) | 3.53000 | 0.00000 | | |

| Layer | Material | Refractive Index | Extinction Coefficient | Optical Thickness (FWOT) | Physical Thickness (nm) |
|---|---|---|---|---|---|
| Medium | Air | 1.00000 | 0.00000 | | |
| 1 | Ag | 0.48000 | 14.40000 | 0.00720000 | 30.00 |
| 2 | SiO2 | 1.43807 | 0.00000 | 1.07855369 | 1500.00 |
| 3 | Ag | 0.48000 | 14.40000 | 0.00720000 | 30.00 |
| Substrate | Glass | 1.49447 | 0.00000 | | |

Figure 6A:
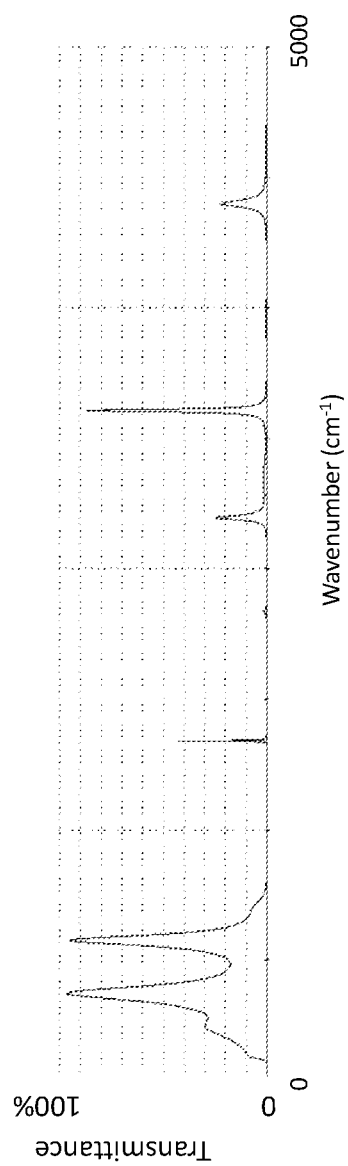
FIG. 6A shows the transmission spectrum of the thin film etalon described in FIG. 5A.
Figure 6B:
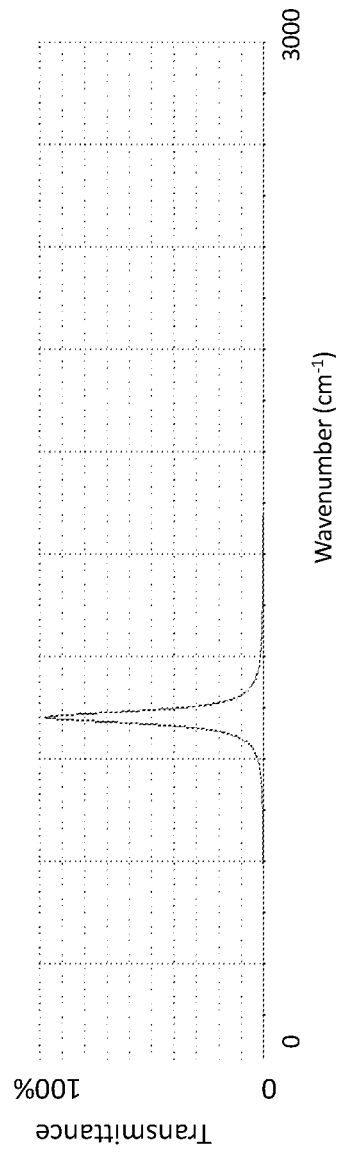
FIG. 6B is the transmission spectrum of the silver etalon described in FIG. 5B.

The resulting transmission spectra are shown in FIG. 6A, B. By comparing the spectrum in FIG. 6A with the spectrum of CO2 in FIG. 4, it can be seen that the relative transmission peak of the 20 layer stack etalon is the very narrow one at ~2350 cm-1. The other peaks in the transmission spectrum of the etalon are not important and will create little interference, as explained layer. The transmission peak of the silver etalon in FIG. 6B is somewhat broader, but does not have spurious transmission peaks. Noteworthy is that the fraction of radiation transmitted through the 20 layer stack etalon is 40× greater than that of the silver etalon at about the 2300 wavenumbers.

FIG. 7A shows the $CO_2$ spectrum superimposed on the 20 layer stack etalon transmission for 0 degrees incidence of light on the etalon (right peak). FIG. 7A also shows the $CO_2$ spectrum superimposed on the 20 layer stack etalon transmission at 10 degrees incidence of light on the etalon (left peak). At 0 degree incidence, the passband (transmission wavelength) of the etalon is centered at ~2354 cm-1. As the etalon is gradually tilted, its passband will increase (continuously). At 10 degrees the passband is centered at ~2342 cm-1. (The passband at intermediate angles is not shown for clarity). The passband of the etalon changes with angle because the effective thickness of the layer increases with increasing angle. FIG. 7B shows the CO2 spectrum superimposed on the Ag mirrored etalon.

Two important observations can be made. (1) Significant tuning of the transmission wavelength can be achieved with a small tilt of the etalon, without degradation of the passband. (2) The width of the etalon transmission band is sufficiently narrow to resolve the individual lines in the $CO_2$ spectrum. For higher molecular weight molecules, the passband width shown here will not be sufficient, because the line spacing in the molecular spectrum scales roughly inversely with the molecular weight. For smaller molecules (e.g. CO) the spacing will be larger and the resolving power of this etalon will be more than adequate. FIG. 7B shows the $CO_2$ spectrum overlaid with that of the silver etalon. Although the etalon spectral width is considerably broader than the lines in the $CO_2$ spectrum, the resolution of the etalon in this case is sufficient to resolve the coarse structure of the $CO_2$ spectrum. This level of resolution will be adequate in many applications.

It should be noted that with more layers and further optimization, higher resolution etalons can be made. These will be higher cost and lower yield during manufacturing.

A gas sensing device is described. The device may include a broad spectrum infrared emitter, a sample of a gas, a multilayer etalon with a transmission profile that transmits wavelengths of light from the broad spectrum infrared emitter within a passband, a positioner that adjust the position of the etalon with respect to the emitter, so as to tune the passband of the etalon, and a detector that detects the amount of light transmitted through the etalon. The etalon may be designed to have a transmission peak at about 2300 wavenumbers, and the gas sample comprises carbon dioxide. The passband of the etalon may be tunable over about 20 wavenumbers by rotating the etalon about 10 degrees about an axis perpendicular to its optical axis.

The list of gas species to which this device is appropriate is virtually endless. For example, the gas sample may comprise at least one of carbon dioxide, carbon monoxide, sulfur, or XY, where X and Y are halogen atoms and X≠Y or if X=Y, X and Y are different isotopes of the same halogen atom, HX where X is a halogen atom, HD, $O_2$, where each oxygen atom is a different isotope, $N_2$, where each nitrogen atom is a different isotope, NO, NS, or SO. The etalon is designed to have a transmission peak at around a feature in the absorption band of the gas sample. The detector may be a photodiode and the emitter may be a vertical cavity surface emitting laser or the sun. The passband of the etalon may be about 2-30 wavenumbers wide.

The sensor may further comprise a reflector and partial reflector in a path between the broad spectrum infrared emitter and the detector. The emitter may be a laser diode and the detector may be a photodiode. The front reflector and the back reflector may comprise a multipass optical cavity around the gas sample. The turning mirror may comprise a half-silvered mirror. The total volume of the gas sensing device is less that about 5 mm^3.

A method of sensing a gas is also disclosed. The method may comprise providing radiation from a broad spectrum emitter, which may be the sun, applying the radiation to a sample of a gas, transmitting the radiation in the passband of a multilayer etalon with a transmission profile that transmits wavelengths of light from the broad spectrum infrared emitter within a passband, and detecting the amplitude of the transmitted radiation.

The method may further comprise adjusting the position of the etalon with respect to the emitter, so as to tune the passband of the etalon. The etalon may be designed to have a transmission peak at about 2300 wavenumbers, and the gas sample comprises carbon dioxide. The emitter may be a laser diode and the detector may be a photodiode. The etalon may be designed to have a transmission peak at about 2300 wavenumbers, and the gas sample comprises carbon dioxide. The passband of the etalon may be tunable over about 20 wavenumbers by rotating the etalon about 10 degrees about its vertical axis. The gas sample may be at least one of carbon dioxide, hydrogen, fluorine, oxygen and nitrogen, though this list is not exhaustive and there may be many others. The etalon may designed to have a transmission peak at around a feature in the absorption band of the gas sample.

The detector may be a photodiode and the emitter may be a vertical cavity surface emitting laser. The passband of the etalon may be about 2-20 wavenumbers wide.

While various details have been described in conjunction with the exemplary implementations outlined above, various alternatives, modifications, variations, improvements, and/or substantial equivalents, whether known or that are or may be presently unforeseen, may become apparent upon reviewing the foregoing disclosure. Furthermore, although the embodiment described herein pertains primarily to an gas sensor, it should be understood that various other devices may be used with the systems and methods described herein. Accordingly, the exemplary implementations set forth above, are intended to be illustrative, not limiting.

What is claimed is:

1. A gas sensing device, comprising:
 a broad spectrum infrared emitter;
 a sample of a gas;
 a multilayer etalon with a transmission profile that transmits wavelengths of light from the broad spectrum infrared emitter within a passband;
 a positioner that adjusts a position of the multilayer etalon with respect to the broad spectrum infrared emitter, so as to tune the passband of the multilayer etalon; and
 a detector that detects an amount of light transmitted through the multilayer etalon, wherein the multilayer etalon comprises a plurality of dielectric thin films, wherein the plurality of dielectric thin films are disposed one on top of another in a stack wherein the stack includes both metal thin films and dielectric thin films.

2. The gas sensing device in claim 1, wherein the broad spectrum emitter is the sun and wherein the sample of a gas is earth's atmosphere.

3. The gas sensing device in claim 1, wherein the positioner modulates an angle of the multilayer etalon, and wherein the broad spectrum infrared emitter is tunable.

4. The gas sensing device in claim 1, wherein the detector comprises at least one of Si, Ge, InSb, SiGe solid state photodetector, and wherein an output wavelength of the broad spectrum infrared emitter is tunable.

5. The gas sensing device of claim 1, wherein the multilayer etalon is designed to have a transmission peak in a range around 2300 wavenumbers, wherein the broad spectrum infrared emitter is tunable through the range, and wherein the sample of the gas comprises carbon dioxide.

6. The gas sensing device of claim 1, wherein the center frequency of the passband of the etalon is tunable within a range of 20 wavenumbers by rotating the multilayer etalon about 10 degrees about its vertical axis.

7. The gas sensing device of claim 1, wherein the sample of the gas comprises at least one of carbon dioxide, hydrogen, fluorine, oxygen, and nitrogen, and the multilayer etalon is designed to have a transmission peak at around a feature in an absorption band of the sample of the gas.

8. The gas sensing device of claim 1, wherein the detector comprises a photodiode, and the broad spectrum infrared emitter comprises a vertical cavity surface emitting laser.

9. The gas sensing device of claim 1, wherein the passband of the multilayer etalon is about 20 wavenumbers wide, and peaks at about 2300 wavenumbers.

10. The gas sensing device of claim 9, further comprising:
 a front reflector and a back reflector, which define a multipass optical cavity around the sample of the gas; and
 a half-silvered turning mirror disposed within the multipass optical cavity.

11. The gas sensing device of claim 1, wherein a total volume of the gas sensing device is less than 5 mm$^3$.

12. A method of sensing a gas, comprising:
 providing radiation from a broad spectrum infrared emitter;
 applying the radiation to a sample of a gas;
 transmitting the radiation in a passband of a multilayer etalon with a transmission profile that transmits wavelengths of light from the broad spectrum infrared emitter within a passband; and
 detecting an amplitude of the transmitted wavelengths of light,
 wherein the multilayer etalon comprises a plurality of dielectric thin films,
 wherein the plurality of dielectric thin films are disposed one on top of another in a stack, and
 wherein the stack includes both metal thin films and dielectric thin films.

13. The method of claim 12, further comprising adjusting a position of the etalon with respect to the broad spectrum infrared emitter, so as to tune the passband of the multilayer etalon.

14. The method of claim 12, wherein the multilayer etalon is designed to have a transmission peak at about 2300 wavenumbers, and the sample of the gas comprises carbon dioxide.

15. The method of claim 12, wherein the broad spectrum infrared emitter is a laser diode and the detector is a photodiode.

16. The method of claim 12, wherein the center frequency of the passband of the multilayer etalon is tunable within a range of 20 wavenumbers by rotating the multilayer etalon about 10 degrees about its vertical axis, and wherein the passband of the multilayer etalon is about 2-20 wavenumbers wide.

17. The method of claim 12, wherein the sample of the gas comprises at least one of carbon dioxide, hydrogen, fluorine, oxygen hydrofluoric acid, hydrochloride acid, methane, ethane, propane, methanol, ethanol, propanol, H2S, OCS, SO2, acetylene, ethylene, chloromethane, fluormethane, and nitrogen, and the multilayer etalon is designed to have a transmission peak at around a feature in an absorption band of the sample of the gas, and wherein the detector comprises a photodiode, and the broad spectrum infrared emitter comprises a vertical cavity surface emitting laser.

\* \* \* \* \*